(12) United States Patent
Sakai et al.

(10) Patent No.: US 7,119,211 B2
(45) Date of Patent: Oct. 10, 2006

(54) PROCESS FOR PREPARING OPTICALLY ACTIVE 3-(METHYLAMINO)-1-(2-THIENYL) PROPAN-1-OL AND INTERMEDIATES FOR PREPARATION

(75) Inventors: Kenichi Sakai, Kitaibaraki (JP); Rumiko Sakurai, Kitaibaraki (JP); Atsushi Yuzawa, Kitaibaraki (JP); Kaoru Hatahira, Kitaibaraki (JP)

(73) Assignee: Yamakawa Chemical Industry Co., Ltd., Tokyo (JP)

( * ) Notice: Subject to any disclaimer, the term of this patent is extended or adjusted under 35 U.S.C. 154(b) by 190 days.

(21) Appl. No.: 10/947,333

(22) Filed: Sep. 23, 2004

(65) Prior Publication Data

US 2006/0063943 A1   Mar. 23, 2006

(51) Int. Cl.
C07D 333/12 (2006.01)
C07D 333/22 (2006.01)

(52) U.S. Cl. .............................. 549/75; 549/76; 549/77

(58) Field of Classification Search .................. 549/75, 549/76, 77
See application file for complete search history.

(56) References Cited

U.S. PATENT DOCUMENTS 6,723,745 B1 *  4/2004  Nishi et al. ................. 514/438
6,753,344 B1 *  6/2004  Talley et al. ................ 514/438
6,800,759 B1 * 10/2004  Valeriano et al. ........... 546/114
6,992,110 B1 *  1/2006  Kranzler et al. ............ 514/620
7,005,452 B1 *  2/2006  Deregnaucourt et al. ... 514/620
7,045,341 B1 *  5/2006  Kamal et al. ............... 435/280

* cited by examiner

Primary Examiner—Deborah C. Lambkin
(74) Attorney, Agent, or Firm—Posz Law Group, PLC; R. Eugene Varndell, Jr.

(57) ABSTRACT

Disclosed is a process for commercial preparation of 3-(methylamino)-1-(2-thienyl)propan-1-ol (hereinafter abbreviated as "MMAA") of the formula below:

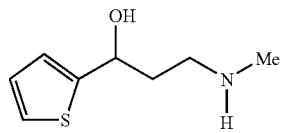

The process is carried out by the diastereomeric salt formation method using optically active mandelic acid or its derivatives, or an optically active tartaric acid derivative as the resolving agent. The product compound, diastereomeric satls, is useful as the intermediate for producing pharmaceuticals, such as duloxetine.

7 Claims, No Drawings

PROCESS FOR PREPARING OPTICALLY ACTIVE 3-(METHYLAMINO)-1-(2-THIENYL) PROPAN-1-OL AND INTERMEDIATES FOR PREPARATION

BACKGROUND OF THE INVENTION

1. Field in the Industry

The present invention concerns a process for preparing optically active 3-(methylamino)-1-(2-thienyl)propan-1-ol (hereinafter abbreviated as "MMAA"). The present invention concerns also novel diastereomeric salts obtained as the intermediates in the process for preparing the optically active MMAA. The optically active MMAA prepared by the present process is an important intermediate for synthesis of pharmaceuticals, particularly, for a new drug "Duloxetine" (EP273658) which is expected to be a useful pharmaceutical for treating depression and urinary incontinence.

2. Prior Art

For the preparation of Duloxetine the following synthesis route has been known. Optically active 3-(dimethylamino)-1-(2-thienyl)propan-1-ol (herein-after abrreviated as "DATP") is condensed with a naphthalene to form a naphthyl derivative, followed by demethylation to give Duloxetine (*Chirality in industry II*, p. 101–104 (1997); John Wiley & Sons: Yew York).

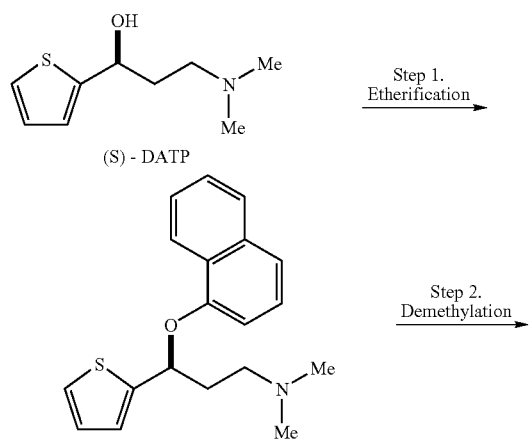

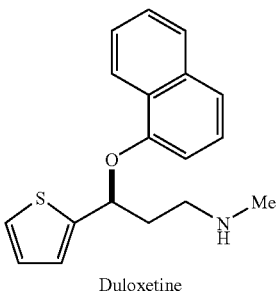

Duloxetine

As the methods to carry out the above demethylation there has been known to treat the naphthyl derivative with trichloroacetyl chloride (Japanese Patent Disclosure 04-226948 (1992), *Tetrahedron Lett.*, 31(49), 7101 (1990)), or with phenoxycarbonyl chloride (Japanese Patent Disclosure 07-188065(1995)). These known methods, however, have such drawbacks that trichloroacetyl chloride itself is harmful, that the yield of synthesis is low, and that partial racemization occurs during the reaction. In other words, as far as the preparation method through the dimethylation route is applied, it cannot be avoided that the yield is low and the optical purity decreases due to the racemization during the step.

On the other hand, if MMAA, which is demethylated derivative of DATP, is used as the intermediate for preparation of Duloxetine, demethylation step is unnecessary, and it can be expected that condensation of MMAA with a naphthalene compound according to the known methods (such as that of EP273658) may easily give Duloxetine without any deterioration caused by demethylation step, as shown below.

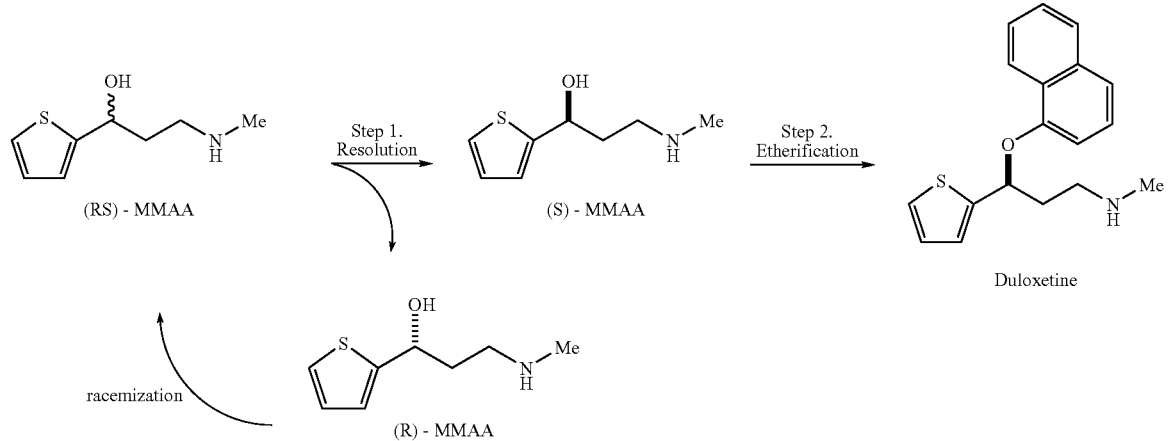

In case where the optical resolution accompanies the preparation of Duloxetine, recovered (R)-MMAA from the mother liquor can be racemized by an ordinary racemization method and recycled to the next batch of the resolution step.

To date, however, there has not been known process for preparing optically active MMAA by optical resolution. Having noted this fact the inventors made research intensively on the optical resolution of MMAA and succeeded to develop a new resolution process suitable for a commercial scale production.

SUMMARY OF THE INVENTION

The object of the present invention is to utilize the inventors' knowledge on the process for preparing optically active MMAA, which is an important intermediate for producing pharmaceuticals, and to provide a process for preparing optically active MMAA, using a less expensive resolving agents of which both the antipodes are easily available, which gives either of (S)-MMAA with high optical purities, and which is thus advantageous in industrial application.

The diastereomeric salts formed as the intermediates during preparation of the above optically active MMAA are novel compounds, and to provide these intermediates are also a part of object of this invention.

The process for preparing the optically active MMAA according to the present invention comprises using optically active mandelic acid or its derivatives or optically active tartaric acid or its derivatives as the resolving agents to resolve the (RS)-MMAA of the following formula by the diastereomeric salt formation method.

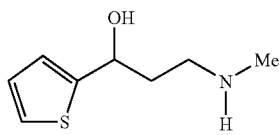

DETAILED EXPLANATION OF THE PREFERRED EMBODIMENTS

It is known that racemic DATP, (which is a compounds similar to MMAA), can be resolved with optically active mandelic acid (*Chirality in Industry II*, p. 101–104 (1997); John Wiley & Sons: Yew York) However, according to the inventors' experiments, racemic MMAA could not be resolved under the known conditions applied for DATP, and even no diastereomeric salt crystal was precipitated.

The inventors studied the reason of the above discussed difference, and speculated that the above difference was caused by the difference in hydrogen-bonding abilities between MMAA, a secondly amine, and DATP, a tertiary amine. In order to increase the hydrogen-bonding ability of the secondary amine possessing one more proton than the tertiary amine, water was added to the resolution medium. The trial was successful and it was observed that MMAA successfully formed a less soluble diastereometric salt with mandelic acid and water molecule. Furthermore, it was also found that the similar optical resolution can be carried out by using mandelic acid derivatives or tartaric acid derivatives as a resolving agent, and thus, the present invention was completed.

The present process for preparing a respective diastereometric salt is carried out by a diastereomeric salt formation method. The above mentioned racemic MMAA is treated with a resolving agent in a reaction media to form a less-soluble diastereomeric salt, then one of the salts is separated from the mother liquor and decomposed to recover the optically active MMAA, and the resolving agent used, the optically active mandelic acid derivatives or optically active tartaric acid derivatives.

The optically active mandelic acid or its derivatives have the above mentioned general formula, in which, alkyl radicals expressed by $R^1$ are alkyl groups of straight or branched chain such as methyl, ethyl, isopropyl and tert.-butyl; alkoxy groups expressed by $R^1$ are those of straight or branched chain such as methoxy, ethoxy, isopropoxy and tert.-butoxy; halogen atoms expressed by $R^1$ are fluorine, chlorine and bromine atoms.

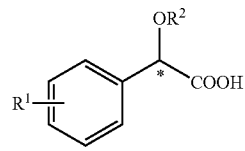

The alkyl groups expressed by $R^2$ are alkyl groups of straight or branched chain such as methyl, ethyl, isopropyl and tert.-butyl; the acyl groups expressed by $R^2$ are those of alkyl carbonyl such as acetyl, propionyl, isobutyryl and pivaloyl.

Examples of the optically active mandelic acid derivatives are mandelic acid, 2-metylmandelic acid, 2-chloromandelic acid, 3-chloromandelic acid, 4-methoxymandelic acid, O-acetylmadelic acid and α-methoxyphenylacetic acid. Among them, mandelic acid and α-methoxyphenylacetic acid are the most preferable.

As the optically active tartaric acid derivatives there are exemplified the following O,O'-dibenzoyltartaric acid of the formula:

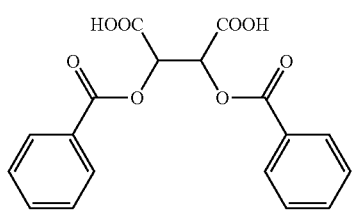

and O,O'-di-p-toluoyltartaric acid of the formula

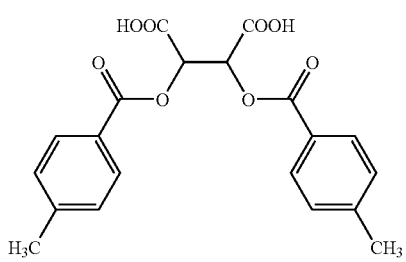

and some other compounds such as O,O'-acetyl-tartaric acid, O,O'-di-p-chlorobenzolyltartaric acid, O,O'-dinaphthoyltartaric acid. Preferable ones are O,O'-di-p-toluoyetartaric acid and O,O'-di-p-toluoyetartaric acid.

Formation of the diastareomeric salts is carried out in a suitable reaction medium. Preferable medium for the reaction of diastereomeric salt formation is such one that the less-soluble salt of the diastereomeric salts easily precipitates therefrom, and that dissolves well the more-soluble salt. The reaction medium is chosen from this point of view.

As the suitable reaction medium water is mentioned first. Then, alcohols such as methanol, ethanol, 1-propanol and 2-propanol; ethers such as diethyl ether, methyl tert-butyl ether and tetrahydrofuran; acetic acid; esters such as methyl acetate, ethyl acetate; isopropyl acetate and butyl acetate; ketones such as acetone, methyl ethyl ketone and methyl isobutyl ketone; nitrites such as acetonitrile; halogenated hydrocarbons such as methylene chloride, chloroform and 1,2-dichloroethane; and aromatic hydrocarbons such as benzene, toluene and xylenes. The solvents may be used solely or in combination of two or more of them.

Thus a wide variety of reaction medium can be used. Based on the fact that water or water containing lower alcohols (or mixtures thereof) give favorable results. Namely, protic solvents seem to be suitable. As described in the working example below, when mandelic acid is used as the resolving agent, it is necessary to use water or a water-containing medium. The resolution results are influenced by the amount of the medium used. Suitable range of the amount of the medium is strictly depending on the sort of the medium.

The amount of the resolving agent used should be in a range of 0.3–1.1 moles, preferably 0.4–1.0 moles per one mole of (RS)-MMAA. Preferable molar ratio varies depending on a sort of the resolving agent and a reaction media.

There is no particular restriction on the manner of proceeding formation of the diastereomeric salts. An ordinary example is to charge the starting material, the racemic form, into the reaction medium and dissolve the material by heating at the temperature below the boiling point of the medium under ambient pressure, and to add the resolving agent may be done either at once or continuously. It is not always necessary to completely dissolve the racemic material in the medium, because formation of the diastereomeric salt may proceed even if the resolving agent is partially added to the system and even if the rest of racemic form is suspended therein. The resolving agent may also be added in the form of a solution in the reaction medium.

Results of the optical resolution by the diastereomeric salt formation method are determined by the difference of solublities of the more-soluble and the less-soluble salts. In the optical resolution according to the present invention there have been found some suitable combinations of polarity and amount of the reaction medium, and a sort and an amount of the resolving agent. If necessary, optimum resolution conditions can be found by some additional experiments while referring the working examples described below.

The reaction mixture in which the diastereomeric salts are formed is filtered or centrifuged to obtain the less-soluble diastereomemic salt. Decomposition of the salts obtained may be done by adding a strong acid or a strong base. Practical operation is to add an inorganic strong base such as sodium hydroxide into the diatereomeric salt in a mixture of organic solvent and water, and then, the optically active MMAA is extracted with an organic solvent. The organic solvent to be used are those having less compatibility with water such as toluene, ethyl acetate, diethyl ether and methyl tert-butyl ether.

The solubility of the optically active MMAA is relatively low in aromatic hydrocarbons compared with that of the racemic form. Utilizing this property, the optically active MMAA can be purified by recrystallization. The diastereomeric salts is decomposed with alkaline in an aromatic hydrocarbons such as toluene followed by adding water. The reaction mixture is settled to separate an organic (toluene) layer. The Organic layer is concentrated and cooled to give purified crystals. Even if the optical purity of the crude crystal(MMAA) is 90% or so, recrystallization gives purified crystal(MMAA) having an optical purity higher than 99%.

The process according to the present invention makes it possible to prepare either of (R)-form or (S)-form of MMAA as desired. The present process using resolving agent which is easily available and inexpensive gives the optically active MMAA with high optical purity and good yield, and therefore, it can be practiced advantageously in providing with low cost high optical purity.

EXAMPLES

Determination of the optical purity of the MMAA in the following examples was carried out by HPLC under the conditions below.

Column: "SHISEIDO Chiral CD-Ph" 50 µm 4.6 m I.D.×250 mm
Mobile Phase: 0.2M sodium perchlorate aqueous solution/ acetonitrile (70/30)
Flow Rate: 1.0 ml/min.
Column Temperature: 35° C.
Detector: JASCO "UV-970", wave length 235 nm
Retention: (R)-MMAA 11 min., (S)-MMAA 13 min.

Example 1

Preparation of (S)-MMAA.(S)-Mandlic Acid Monohydrate (Optical Resolution of MMAA using Optically Active Mandelic Acid)

(RS)-MMAA 100 g (0.584 mol) was charged to 2-butanol 190 g, and (S)-mandelic acid 89 g (0.584 mol) was added (molar ratio 1:1), and further, water 21 g (1.17 mol) was added thereto. The mixture was heated to dissolve the salts. Then, the resulting solution was cooled to 35° C., and a small amount of previously prepared seed crystals of (S)-MMAA.(S)-mandlic acid monohydrate was added to the solution and cooled to 20° C. The precipitated crystal was filtered and dried to give 83.2 g of (S)-MMAA.(S)-mandlic acid monohydrate. The yield of the salt based on the (RS)-MMAA was 83.4%, and the optical purity of the salt obtained was 75.2% de.

The crude salt was recrystallized from a mixed solvent of water and 2-butanol. Recrystallized salt, (S)-MMAA.(S)-mandelic acid monohydrate was 66.1 g and the optical purity thereof was 95.3% de. The yield of the salt based on the (S)-MMAA in the starting (RS)-MMAA was 66.4%.

m.p.: 69.9–71.0° C.
Rotation: $[\alpha]_D^{20}$ +26.4° (c 1.0, EtOH)
Moisture (water content): 5.27% (Karl-Fischer Titretion)
IR (KBr) cm$^{-1}$: 3470, 3208, 1618, 1586, 1491, 1051, 701.
$^1$H-NMR (CDCl$_3$, 400 MHz): δ 7.37–7.40(m, 3H), 7.22–7.25(m, 2H), 7.17(d, J=5.2 Hz, 1H), 6.96(dd, J=3.2, 5.2 Hz, 1H), 6.90(d, J=3.2 Hz, 1H), 4.89(dd, J=4.8, 8.0 Hz, 1H), 4.60(s, 1H), 2.86–2.91(m, 2H), 2.44(s, 3H), 1.92–1.99 (m, 2H).

Example 2

Preparation of (S)-MMAA

After addition of water to the diastereomeric salt prepared in Example 1, 30% sodium hydroxide aqueous solution was added and the mixture was shaken with 2-butanol. The resulting organic layer was separated and concentrated under reduce pressure. The concentrate thus obtained was added to toluene and dissolved by heating, then gradually cooled to 45° C. A small amount of seed crystal of (S)-MMAA previously prepared was added and the solution was cooled to ambient temperature. The precipitated crystals were filtered and dried. (S)-MMAA of 43.8 g was obtained. The yield based on the crude salt was 66% and the optical purity was 99.9% ee.

m.p.: 70.5–73.0° C.
Rotation: $[\alpha]_D^{20}$ –16.5° (c 1.0, EtOH)
IR (KBr), cm$^{-1}$: 3384, 3284, 1489, 1303, 1178, 1110, 1085, 709
$^1$H-NMR (d$_6$-DMSO, 400 MHz): δ 7.20(d, J=5.2 Hz, 1H), 6.96(dd, J=3.2, 5.2 Hz, 1H), 6.92(d, J=3.2 Hz, 1H), 5.17(dd, J=3.2, 8.0 Hz, 1H), 2.94(ddd, J=3.6, 5.6, 8.0 Hz, 1H), 2.84(ddd, J=3.2, 9.2, 12.0 Hz, 1H), 2.42(s, 3H), 1.85–2.00 (m, 2H).

Example 3

Optical Resolution of MMAA with Optically Active α-Methoxyphenylacetic Acid

To the (RS)-MMAA 1.00 g (5.84 mmol) was added to 2-propanol 5 g and (R)-α-methoxyphenylacetic acid 0.96 g (5.84 mmol, molar ratio 1:1). After addition of water 0.1 g, the mixture was heated to dissolve the solids. The resulting solution was gradually cooled to 25° C., and a small amount of previously prepared (S)-MMAA.(R)-α-methoxyphenylacetic acid was added as the seed crystals. The solution was cooled to 20° C. The precipitated crystals were filtered and dried. Crude (S)-MMAA.(R)-α-methoxyphenylacetic acid was 0.51 g. The yield based on the (S)-MMAA in the (RS)-MMAA was 52%, and the optical purity of the salt was 73.3% de. The salt was recrystallized from 2-propanol to give pure (S)-MMAA.(R)-α-methoxyphenylacetic acid. The optical purity of the MMAA in the pure salt was 100% de.

m.p.: 106.0–106.8° C.
Rotation: $[\alpha]_D^{20}$ –61.3° (c 1.0, EtOH)
IR (KBr) cm$^{-1}$: 3316 3062, 2876, 1620, 1567, 1395, 1196, 1093, 1073, 700

Example 4

Optical Resolution of MMAA with Optically Active O,O'-di-p-toluoyltartaric Acid (RS)-MMAA 1.00 g (5.84 mmol) was charged into ethanol 5 g, and (2R,3R)-(–)-O,O'-di-p-toluoyltartaric acid 2.26 g (5.84 mmol) was added thereto (molar ratio 1:1). The mixture was heated to dissolve the solids. The resulting solution was gradually cooled to 39° C. A small amount of previously prepared (S)-MMAA.(2R,3R)-(–)-O,O'-di-p-toluoyltartaric acid was added as seed crystals, and the solution was cooled to 20° C. The precipitated crystal was filtered and dried. (S)-MMAA.(2R,3R)-(–)-O,O'-di-p-toluoyltartaric acid 153 g was obtained. The yield based on the (S)-MMAA in the (RS)-MMAA was 94%, and the optical purity of the obtained salt was 52.9% de.

Example 5

Optical Resolution of MMAA with Optically Active O,O'-Dibenzoyltartaric Acid (RS)-MMAA 1.00 g (5.84 mmol) was charged into ethanol 5 g, and (2R,3R)-(–)-O,O'-dibenzoyltartaric acid 2.09 g (5.84 mmol) was added thereto (molar ratio 1:1). The mixture was heated to dissolve the solids. The resulting solution was gradually cooled to 39° C. A small amount of previously prepared (S)-MMAA.(2R,3R)-(–)-O,O'-dibenzoyltartaric acid was added as the seed crystal, and the solution was cooled to 20° C. The precipitated crystal was filtered and dried to give (R)-MMAA.(2R,3R)-(–)-O,O'-dibenzoyltartaric acid 2.29 g. The yield based on the (R)-MMAA in the (RS)-MMAA used as the material was 148%, and the optical purity of the salt was 13.1% de.

Comparative Example

Preparation of (S)-MMAA.(S)-Mandelic Acid in Case Where the Reaction Medium Contains No Water (RS)-MMAA 100 g (0.584 mol) was charged into 2-butanol 190 g, and (S)-mandelic acid 89 g (0.584 mol) was added thereto (molar ratio 1:1). The mixture was heated to dissolve the solids. When the resulting solution was cooled down to ambient temperature, no crystal was precipitated.

We claim:

1. A process for preparation of optically active 3-(methylamino)-1-(2-thienyl)propan-1-ol (herein-after abbreviated as "MMAA"), comprising:
optical resolution of (RS)-MMAA of the formula 1 below:

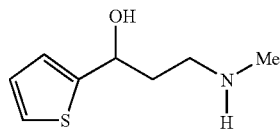

by diastereomeric salt formation method using a resolving agent selected from optically active mandelic acid, its derivatives, optically active tartaric acid and its derivatives.

2. The process according to claim 1, wherein the optically active mandelic acid or its derivatives of the formula below is used as the resolving agent:

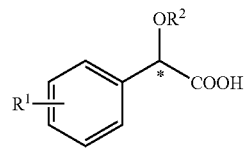

wherein R$^1$, is hydrogen atom, alkyl group, alkoxy group, nitro group or halogen atom; R$^2$ is hydrogen atom, alkyl group or acyl group; and *(asterisk) indicates the position of the asymmetric carbon atom; and wherein a protic solvent is used as the reaction medium.

3. The process according to claim 2, wherein optically active mandelic acid is used as the resolving agent, and water or a mixture of water and a lower alcohol is used as the reaction medium.

4. The process according to claim 1, wherein optically active O,O'-dibenzoyltartaric acid of the formula below:

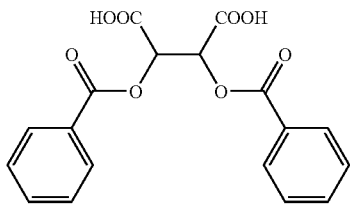

is used as the resolving agent.

5. The process according to claim 1, wherein optically active O,O'-di-p-toluoyltartaric acid of the formula below:

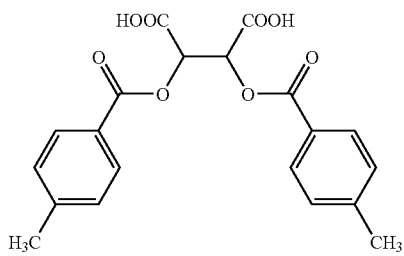

is used as the resolving agent.

6. (S)-MMAA•(S)-mandelic acid monohydrate of the formula below:

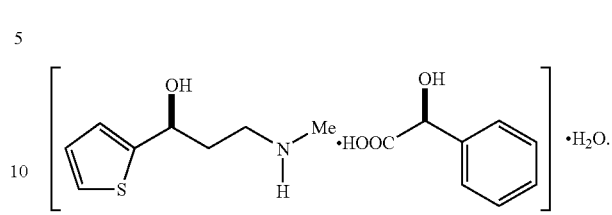

7. (S)-MMAA•(R)-α-methoxyphenylacetic acid of the formula below:

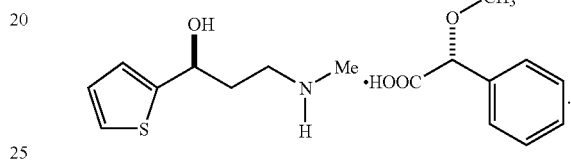

* * * * *